US011490868B2

United States Patent
König et al.

(10) Patent No.: US 11,490,868 B2
(45) Date of Patent: Nov. 8, 2022

(54) METHOD FOR SUPERIMPOSING A TWO-DIMENSIONAL X-RAY IMAGE ON PROJECTIVE IMAGES OF THREE-DIMENSIONAL STRUCTURES

(71) Applicant: Ziehm Imaging GmbH, Nuremberg (DE)

(72) Inventors: Thomas König, Nuremberg (DE); Klaus Hörndler, Nuremberg (DE); Marc Kachelriess, Nuremberg (DE); Michael Knaup, Reichenschwand (DE)

(73) Assignee: Ziehm Imaging GmbH, Nuremberg (DE)

( * ) Notice: Subject to any disclaimer, the term of this patent is extended or adjusted under 35 U.S.C. 154(b) by 0 days.

(21) Appl. No.: 17/183,192

(22) Filed: Feb. 23, 2021

(65) Prior Publication Data
US 2021/0267566 A1  Sep. 2, 2021

(30) Foreign Application Priority Data

Feb. 27, 2020 (DE) .......................... 102020001314.7

(51) Int. Cl.
*A61B 6/00* (2006.01)
*G06T 7/11* (2017.01)
(Continued)

(52) U.S. Cl.
CPC .......... *A61B 6/5235* (2013.01); *A61B 6/4441* (2013.01); *A61B 6/481* (2013.01); *A61B 6/504* (2013.01); *A61B 6/505* (2013.01); *A61B 6/5247* (2013.01); *G06T 5/50* (2013.01); *G06T 7/11* (2017.01); *G06T 17/00* (2013.01); *G16H 30/40* (2018.01); *G06T 2200/04* (2013.01);
(Continued)

(58) Field of Classification Search
CPC ............................................ G06T 2207/30101
See application file for complete search history.

(56) References Cited

U.S. PATENT DOCUMENTS

2006/0188139 A1   8/2006  Khamene et al.
2013/0058555 A1*  3/2013  Miao ................... G06V 20/653
                                                    382/132
(Continued)

OTHER PUBLICATIONS

Search Report for DE Application 10 2020 001 314.7 dated Oct. 30, 2020.

*Primary Examiner* — Ryan McCulley
(74) *Attorney, Agent, or Firm* — Knobbe Martens Olson & Bear, LLP (57) ABSTRACT

Medical imaging methods for processing a three-dimensional (3D) image data set with two-dimensional X-ray images from an X-ray machine using a target function. Methods can include providing a 3D image data set of at least one examination zone in which anatomical structures are present, segmenting the image data set to provide a 3D vascular structure model and a 3D bone structure model, recording a first two-dimensional (2D) X-ray image containing at least a portion of the vascular structure and at least a portion of the bone structure, recording a second 2D X-ray image of the examination zone at a different contrast agent concentration, and subtracting the first and second 2D X-ray images to generate a subtraction image. An optimum projective geometry may then be determined using a three-part target function based on the 3D image data and the 2D X-ray images.

12 Claims, 2 Drawing Sheets

(51) Int. Cl.
*G16H 30/40* (2018.01)
*G06T 5/50* (2006.01)
*G06T 17/00* (2006.01)

(52) U.S. Cl.
CPC ............ *G06T 2207/10081* (2013.01); *G06T 2207/10088* (2013.01); *G06T 2207/10116* (2013.01); *G06T 2207/20092* (2013.01); *G06T 2207/20224* (2013.01); *G06T 2207/30101* (2013.01); *G06T 2210/41* (2013.01)

(56) References Cited

U.S. PATENT DOCUMENTS

| | | | |
|---|---|---|---|
| 2018/0221093 A1* | 8/2018 | Hladio | A61B 5/061 |
| 2020/0051258 A1 | 2/2020 | Miao et al. | |
| 2020/0170617 A1* | 6/2020 | de Vaan | G06T 19/003 |
| 2021/0137634 A1* | 5/2021 | Lang | A61B 5/0205 |

* cited by examiner

METHOD FOR SUPERIMPOSING A TWO-DIMENSIONAL X-RAY IMAGE ON PROJECTIVE IMAGES OF THREE-DIMENSIONAL STRUCTURES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure generally relates to medical imaging and more particularly to methods for processing a three-dimensional image data set with two-dimensional X-ray images.

Description of the Related Art

Numerous known medical engineering methods relate to the navigation of objects in the anatomy of a patient.

In such navigation of objects, for example when navigating catheters within vessels, X-ray imaging methods can be used to locate the object. The vessels themselves at first cannot be identified on the X-ray images (fluoroscopic images), which are generally continuously recorded. For this reason, a contrast agent, for example an agent containing an iodine compound or carbon dioxide, is administered to the patient—often repeatedly—which allows the vascular structure to be made visible in the X-ray images.

The combined and/or simultaneous representation of the object, vascular system, and surrounding anatomy is very difficult, as will be shown below.

SUMMARY

Certain problems disclosed herein may be solved according to the present technology by a method with the characteristics specified in the claims that follow. Advantageous embodiments are specified in the dependent claims.

The method according to a first aspect of the present technology for processing a three-dimensional image data set with two-dimensional X-ray images of an X-ray machine includes the following steps: providing a three-dimensional image data set of at least one examination zone in which anatomical structures are present; segmenting the three-dimensional image data set to provide a three-dimensional vascular structure model describing a vascular structure and a three-dimensional bone structure model describing a bone structure; recording a first two-dimensional X-ray image containing at least in part the bone structure and at least in part the vascular structure using a recording geometry and in the presence of a first contrast agent concentration; recording a second two-dimensional X-ray image of the examination zone, which contains a second contrast agent concentration that is different from the first X-ray image, wherein the recording of the second X-ray image takes place using the same recording geometry as the first X-ray image; subtraction of the first and second X-ray images to generate and provide a subtraction image, wherein the subtraction image includes a vascular structure; determining an optimum projective geometry using a three-part target function; wherein a first part of the target function represents a similarity between a forward projection of the bone structure model of the three-dimensional image data set and the bone structure in the first and/or second X-ray images, while varying an assumed projective geometry; wherein a second part of the target function represents a similarity between the forward projection of the vascular structure model of the three-dimensional image data set and the vascular structure of the subtraction image, while varying the assumed projective geometry; and wherein a third part of the target function represents a similarity between all image data of the forward projection of the three-dimensional image data set and all image data of the first and/or second X-ray images, while varying the assumed projective geometry.

DETAILED DESCRIPTION

For a permanent representation of the vascular tree without readministering the contrast agent, a fluoroscopic image of the vascular tree and the surrounding anatomy can first be recorded without contrast agent (mask image). A contrast agent is then injected and X-ray images (filling images) are produced at different, successive points in time, which document the distribution of the contrast agent in the vessel at said different, successive points in time. Repeated injection of contrast agent may be necessary, inter alia, since the contrast agent, for example an agent containing an iodine compound or carbon dioxide, is rapidly diluted in the blood stream, is then transported, for example, into the kidneys (agent containing iodine compound) or the lungs (carbon dioxide), and from there is excreted from the patient. Further, repeated contrast injection may be necessary to represent the vessel in a different perspective that better represents the anatomy to be examined, for example stenosis, or to assess the progress of the operation.

To represent just the vessel structures filled with contrast agent, the mask image is now subtracted (subtraction images) from a part of the filling images taken at different, successive points in time, so that only the vessels filled with contrast agent are represented as a temporal sequence (digital subtraction angiography; DSA). These X-ray images can then be combined to form an X-ray image which represents a vascular tree completely filled with contrast agent (vessel image). This can be done, for example, by a minimum method (in the case of iodine) or a maximum method (in the case of carbon dioxide) in which the lowest or highest grayscale value for each pixel is converted from all subtraction images into the respective pixel of the vessel image over the course of time of the recording. These processes are known from current art and do not need to be explained in greater detail here.

This subtraction image thus permits the visualization of vascular structures including pathologies found therein, such as stenoses, aneurysms, or bleeding into the surrounding tissue. However, the representation of the vessel structures per se does not yet permit navigation of objects therein for the purpose of a medical intervention. A further representation can be produced by means of an inverted vessel image generated from the maximum/minimum method. In a so-called roadmap method, which is known from the prior art, this inverted vessel image can be superimposed with a live X-ray image from the sequence of a DSA recorded in the further course and the navigation of an object in the anatomy of the patient is simplified. This method thus represents, for example, the vascular tree previously extracted in the vessel image in light grayscale levels, but the catheter, which is visible in the live X-ray image of the sequence of the DSA, remains dark, so that it can be recognized during movement in the vessel structure.

If, however, the imaging geometry is changed, for example by tilting the X-ray system used for the imaging, the two-dimensional subtraction image no longer fits the new imaging geometry. As a rule, navigation of objects is not possible in this case without renewed administration of contrast agent. Contrast administration, in particular repeated administration of contrast agent, is a stress on the patient and should be avoided as far as possible.

One possibility for avoiding further administration of contrast agent during an operation in order to visualize low-contrast structures is the use of a three-dimensional image data set recorded before the operation, which provides anatomical data with respect to the bone and vascular structures of the examination zone and thus was obtained while administering a contrast agent. In order to display these structures contained in the three-dimensional data set in the correct position on a two-dimensional live X-ray image for purposes of navigation, a synthetic, two-dimensional projection, also called a forward projection, must first be calculated using a projective geometry which corresponds to the imaging geometry. Determination of the optimum projective geometry is a difficult, non-convex mathematical optimization problem.

The challenge with such a procedure is that the optimum projective geometry determined in this way also corresponds to the actual projective geometry.

When contrast agent-free X-ray images are used to determine the optimum projective geometry between a forward projection generated from the three-dimensional image data set and the recorded two-dimensional X-ray images, bones in particular exhibit a high image contrast in the X-ray images. It is possible to use bones alone to determine a projective geometry in this case, but an additional use of vessels or vessel structures for the similarity is advantageous for a higher accuracy of the similarity.

A method which describes the determination of a coordinate transformation between a three-dimensional image data set and two-dimensional X-ray images is disclosed in document DE102016203857A1. In this case individual registration requirements between the bone and vessel structures from the live X-ray images and the forward projections from the three-dimensional image data set are used.

It may therefore be desirable to make available an improved method for determining a projective geometry between a three-dimensional image data set and two-dimensional X-ray images.

The three-dimensional image data set, which contains anatomical structures of an examination zone, can be prepared by pre-operative computed tomography or magnetic resonance tomography recording. The anatomical structures of the three-dimensional image data set contain at least bone and vascular structures, as well as other structures, for example implant structures and skin edges. Furthermore, the three-dimensional image data set can also be recorded intra-operatively, preferably using intra-operative computed tomography or a C-arm X-ray machine. It is also possible to import the three-dimensional image data set into an internal memory unit, for example an internal image data memory, or an external memory unit, for example a USB stick, an external hard disk, or an online memory to which the X-ray machine implementing the method has access.

The segmentation of the three-dimensional image data set can take place before or after the provision of the three-dimensional image data set, in each case manually, semi-automatically or fully automatically, by means of image processing. The segmentation provides a vascular structure model of the vascular structure from the three-dimensional image data set of the examination zone, and a three-dimensional bone structure model of the bone structure from the three-dimensional image data set of the examination zone is also provided by means of the segmentation. A model of this kind can be, for example, a voxel-by-voxel segmentation of the image regions or a parametric representation of the underlying structures. A parametric representation can be, for example, the description of a vessel by a spline for the central axis of the vessel plus a diameter at any point of the spline.

The first and second X-ray images describe the current position of the patient being examined, who is preferably positioned on a patient bed, and are recorded by means of an X-ray machine, preferably a mobile or stationary fully motor-adjustable C-arm X-ray machine, with corresponding recording geometry, wherein the user can adjust the X-ray machine so that the recording geometry captures the desired examination zone. For example, besides the position of the X-ray machine, the adjustment made may involve the orbital angle, the angulation, the zoom and/or the height adjustment. It is provided that each of the two X-ray images contains a different concentration of contrast agent, for example an iodine-containing compound or carbon dioxide, wherein the concentration of the contrast agent for one of the two X-ray images can also be zero. Such a procedure, as is known, in particular from digital subtraction angiography, makes it possible, by subtraction of the first and second X-ray images, to provide a subtraction image that contains only the zones of the vascular structure that are made visible by the administration of the contrast agent. Generally, the contrast agent is administered via the vascular structure of the patient, so that it primarily represents his vascular structure, in particular the complete vascular structure of the patient. At a low administered contrast agent concentration, the bone structure in particular is represented in the recorded X-ray images. At an administered contrast agent concentration of zero, the bone structures are mainly shown on the respective X-ray image; accordingly, no bone structures are present on the generated subtraction images, since only vascular structures are displayed on the subtraction images.

Subsequently, a projective geometry can be determined which achieves an optimum similarity between a two-dimensional forward projection produced from the three-dimensional image data set, said projection corresponding to a two-dimensional projection plane and the first and/or second X-ray image as well as the subtraction image of the examination zone. This projective geometry can be determined by means of an iterative forward projection of the three-dimensional image data set followed by an algorithmic comparison of said forward projection with the first and/or second X-ray image and the subtraction image.

A three-part target function can be used for this algorithmic comparison, wherein the three parts of the target function are preferably additively linked to one another. In this case, an initial projective geometry, for example a projective geometry predetermined by the system, can be used for determining the projective geometry. This initial projective geometry can be freely selected by a calculating unit of the X-ray machine or set by a user and represents the initialization of the optimization problem that is to be solved.

A first part of the target function represents the similarity of the bone structure model between the forward projection of the three-dimensional image data set and the first and/or second X-ray image. In the algorithmic comparison the forward projection or the vessels, which are segmented and contain contrast agent in the three-dimensional image data set, can be virtually replaced with water, so that the synthetic two-dimensional image only contains bone structures. Preferably, the X-ray image used in the comparison of the bone features does not contain contrast agent and thus mainly contains bone structures.

A second part of the target function describes a similarity between the forward projection from the three-dimensional image data set and the subtraction image which, as is known, for example, from digital subtraction angiography, contains only vessels or vessel structures. Preferably in this case, only the segmented, forward-projected vessels (vessel structure model) are compared with the subtraction image. Preferably, the first or second X-ray image is recorded without contrast agent, so that this recording can be used as a mask image for the substrate image. When different types of contrast agents are used, it is possible to subject either the forward projection or the subtraction image to an inversion of the contrast. Furthermore, if the image quality is poor, the vessels in the forward projection and/or the subtraction image can be processed algorithmically and fully automatically in order to obtain a target function in accordance with the method according to the present technology.

A third part of the target function describes a similarity between the forward projection from the three-dimensional image data set and the first and/or second X-ray image and, in this case, all image data of the recorded X-ray images which relate to the first and second X-ray images and not just to bones and/or vascular structures. Furthermore, for this third part of the target function it is possible to replace the structures filled with contrast agent with water when using X-ray images which were recorded with contrast agent.

A possible form of the target function F can be a linear combination of the three individual parts of the target function ($F_{bone}$—bone parts; $F_{vessel}$—vessel parts, $F_{total}$—all parts):

$$F=\alpha *F_{bones}+\beta *F_{vessel}+\gamma *F_{total}$$

In this case, the real and preferably positive parameters $\alpha$, $\beta$, and $\gamma$ are weighting factors which can regulate the relative influence of the individual components of the target function. The target function F can now be optimized by a mathematical method by varying the projective geometry, preferably by using an iterative method. During each iteration step, the same projective geometry can be assumed for all parts of the target function. Subsequently, on the basis of this assumption, all values of the parts of the target function can be summed up, taking into account the weighting factors, in order to obtain the value of the target function F. In the additional iterations other projective geometries can then be evaluated by the optimization method that is used and after a termination criterion has been reached the projective geometry with the optimum target function value can be presented as the optimum projective geometry.

The optimization method that is used can originate from the class of gradient-based methods (e.g. conjugated gradient, Broyden-Fletcher-Goldfarb-Shanno method (BFGS method)), but can preferably belong to the class of non-convex optimization methods (e.g. simulated annealing, genetic optimization), or a combination of these methods. The target function and thus all its parts can describe a similarity between the first and/or second X-ray image or subtraction image and the synthetic forward projection; in this case, the optimization problem is a maximization problem. Likewise, however, the target function can also describe a dissimilarity; in this case, it is a minimization problem. Depending on the form of the target function, either a minimization or a maximization method can be employed. In principle, however, it is also always possible to transform a similarity to be maximized to a dissimilarity to be minimized, for example by multiplication by "-1," and vice versa. This is particularly important since most optimization methods available in software libraries are formulated and implemented as minimization methods. Thus, for the sake of simplification the discussion below will always concern an optimization problem.

It is possible to determine these parameters as a function of the body region in which an intervention is carried out or to change them accordingly. For example, this can take place in a program, preferably an organ program. Thus, in bone structure regions which have pronounced structural features, for example vertebrae with vertebral processes, the weighting of bone structure similarities can be set significantly higher than the weighting of the vascular structure similarity. Areas which have less pronounced bone structure features, for example the femur, behave differently. In this case, a lower weighting of the bone structure similarity and/or a correspondingly higher weighting of the vascular structures is possible. The weighting factors can be determined automatically, for example by means of an image analysis of the X-ray image and a comparison of the contents with a stored database which specifies the weighting factors with respect to the image contents or their anatomical contents. Furthermore, the coefficients can also be stored in a correspondingly tabulated manner in an organ program. Furthermore, it is possible to set the weighting factors individually by user intervention. It is also possible that the parameters can take on a value of zero, for example by a setting on the part of the user, by deposition in an organ program, or by the method according to the present technology. If a weighting factor is set to zero, parts of the target function for its determination are no longer taken into account.

The value of the target function and its components can be a measure of the quality of the determined projective geometry. The target function can thus be considered as a measure of the similarity, for example a congruence, of the forward projection with the first and/or second X-ray image or of the subtraction image. If the values obtained after completion of the optimization satisfy a threshold value criterion, which is compared with the target function, as can be correspondingly stored in a program, for example an organ program, the calculated projective geometry can be classified as sufficiently correct.

In alternative embodiments, the live X-ray image can be superimposed on the forward-projected vessel structures from the three-dimensional image data set if the value of the target satisfies the preset threshold value criterion. Preferably in this case, the vessels can be represented on the live X-ray image with or without a contour, using the specific projective geometry. The use of such threshold value criteria can be advantageous, since the quality of the projective geometry can be ensured through them. The use of threshold value criteria thus offers the possibility of selecting an alternative method path if the threshold value criterion is not satisfied by the value of the target function.

In alternative embodiments, a repeating recalculation of the first and third parts of the target function (reduced target function), which are always available even without contrast agent administration, thus when a current (live) X-ray image is present, can take place. When contrast agent is no longer present in the examination zone, these two parts of the target function remain unchanged. In the calculation of these two parts of the target function, the recalculated value of the reduced target function is compared with the previous stored value of the target function on the basis of the new recorded X-ray images and the synthetic forward projection previously obtained by means of the projective geometry. In the event that the recalculated value of the reduced target function misses the old value of the target function within a predeterminable tolerance, for example by a factor to be set, which can be determined in a program, for example the organ program, the vessel structure or the vessel contour is no longer represented on the live X-ray image. If the recalculated values of the reduced target function again meet the threshold value, the vessel structure can be superimposed again. Thus, one advantage of the method according to the present technology can be to carry out a continuous automated risk assessment in such a way that the forward projection continues to correspond sufficiently to the actual projective geometry.

In alternative embodiments, it is possible that the value of the target function does not satisfy the threshold value for a certain time interval, for example due to a change in the imaging geometry of the X-ray machine or, for example, due to a change in the position of the X-ray machine or table and thus of the patient that has become apparent. Moreover, the X-ray machine can indicate this and offer the user a redetermination of the projective geometry while re-administering the contrast agent or, alternatively, a switch to an alternative two-dimensional process. The length of this time interval, in which the threshold value cannot be satisfied, can be set in a program, for example in an organ program.

It may come up in alternative embodiments that the compared values of the target function do not satisfy the predetermined threshold value criterion In this case, the X-ray machine can produce an output on a display device, for example a monitor, which prevents the method from continuing and offers the user an alternative, two-dimensional process. This approach minimizes risk.

In alternative embodiments, it is further possible, in a program, for example an organ program, to switch to a two-dimensional process if the target function falls below (in the case of maximization) or exceeds (in the case of minimization) a threshold value of one part of the target function, or of two threshold values of two parts of the target function, or of three threshold values of three parts of the target function.

In an alternative embodiment of the method, at least one measurement field is provided in each live X-ray image. The measurement field can be defined by user intervention or by a system specification in such a way that the measurement field narrowly delimits a possibly time-variable structure, wherein, for example, a movement of the patient can be a time-variable structure. The measurement field is preferably evaluated by adding all pixel values in the measurement field and monitoring the sum value in a sequence of live images. In the event of a local change in the demarcated structure in the measurement field, the sum value of the pixel values will change with respect to the sum value of the previous live X-ray image. Provision is made for monitoring the sum value by setting a threshold value. The threshold value can preferably be set as a fraction of the sum value of the previous live X-ray image. In the event of an above-threshold change in the sum value compared to the previous live X-ray image, an above-threshold shift of position of the demarcated structure is assumed In an alternative embodiment, instead of the one subtraction image, a complete digital subtraction angiography is produced, which represents not just one part but rather the complete vascular structure. In an alternative embodiment, in addition to DSA, a minimum or maximum method can be carried out in a known way. In such a process the lowest (minimum method) or highest (maximum method) grayscale value for each pixel from all subtraction images is converted to the relevant pixel of a vessel image over the timewise course of the recording of the individual subtraction images of the DSA. For the further course of the method, instead of the first or second recording, the vessel image generated by means of the minimum or maximum method is then used instead of the subtraction image.

The present technology will be explained in more detail in the following embodiment examples and with reference to FIG. 1 and FIG. 2.

During the method a continuous X-ray image (e.g., a live X-ray image), with which two-dimensional vessel structures, which were obtained from a previously recorded three-dimensional image data set by projection, are superimposed, can be provided in order to provide the user with a possibility of displaying the vessel structures on a live X-ray image.

Figure 1:
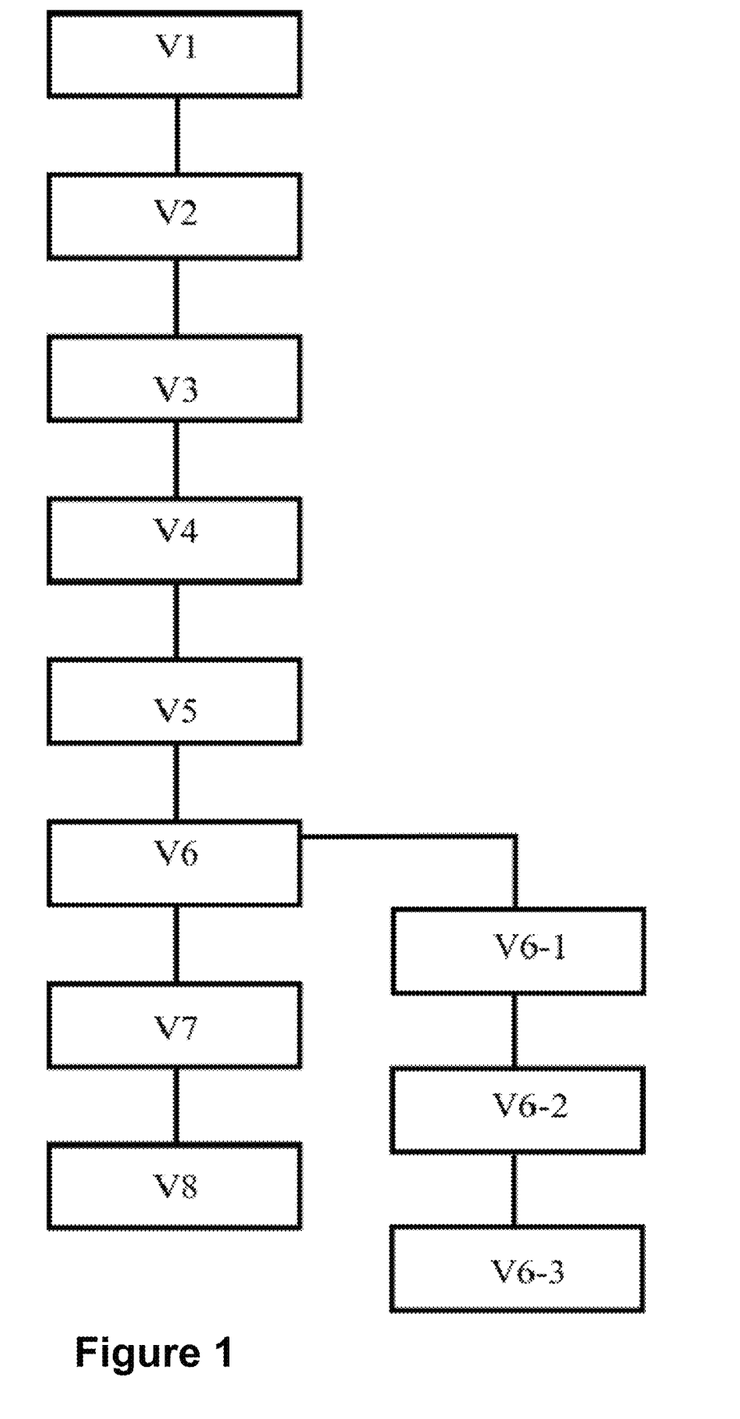
FIG. 1 shows an example of the course of a method according to the present technology.

Referring now to FIG. 1, in method step V1, first the three-dimensional image data set can be recorded, for example by means of computed tomography or magnetic resonance tomography. This three-dimensional image data set comprises the bone structure and the vascular structure of an examination zone. The three-dimensional image data set can be recorded preoperatively or intraoperatively.

In a method step V2, the three-dimensional image data set can then be segmented into bone structure and vessel structure; this can likewise take place immediately after the preoperative recording or before the planned intervention.

After the patient has been positioned with respect to the (e.g., C-arm) X-ray machine, a first X-ray image of the patient can be made in a method step V3, in which a contrast agent can be injected into the patient. However, it is recommended that the first X-ray image in particular be recorded without a contrast agent, so that the first X-ray image primarily shows only the bone structure together with surrounding poorly visible soft structures.

In a method step V4, a second X-ray image of the examination zone can also be made, wherein a contrast agent has been injected into the patient, so that portions of his vascular structure are made visible. In method step V4, digital subtraction angiography can also be carried out. After digital subtraction angiography, a subsequent minimum or maximum method in which the respectively lowest or highest grayscale value for each pixel is converted from all subtraction images into the respective pixel of a vessel image over the course of time of the recording of the digital subtraction angiography, can be used in method step V5. For the further course of the process, the vascular image that is produced, which represents the complete vascular structure, is used.

The subsequent method step V6 comprises the determination of the optimum projective geometry between a forward projection of the three-dimensional image data set and the first X-ray image. The forward projection is a two-dimensional X-ray image synthesized from the three-dimensional image data set. It is also possible to use the second X-ray image instead of the first X-ray image.

In a method step V6-1 the first part of the target function can determine a similarity of the bone structure between the forward projection of the three-dimensional image data set and the first and/or second X-ray image The X-ray image in which the bone structures are mainly shown is preferably used in method step V6-1.

An algorithmic comparison between the forward projection and the first X-ray image can be used for method step V6-1. In this algorithmic comparison, the similarity between a forward projection and the first X-ray image can be maximized, preferably by varying the geometry under which the forward projection is produced, for example by using up to three translations and up to three rotations of the projective geometry. To determine the similarity of the bone structure, it is preferably recommended that the segmented vessel structures containing contrast agent in the forward projection or the segmented vessel structures containing contrast agent in the three-dimensional image data set be virtually replaced with water, so that only bone structures are contained in the forward projection. When determining the similarity of the bone structures, it is recommended that the first X-ray image that is used preferably also does not show contrast agent and thus represents only bone structures.

In method step V6-2, the second part of the target function can be determined. The vessel structures of the vessel image from method step V5 are compared with the forward projection generated from the three-dimensional image data set. The similarity of the vessel structure between the forward projection of the three-dimensional image data set and the first and/or second X-ray image and the subtraction image can likewise be calculated by means of an algorithmic comparison while varying the projective geometry. In the case of determining the similarity of the vessel structure, it is preferably recommended that only the segmented vessels in the forward projection be compared with the subtraction image.

In method step V6-3, a similarity can be determined based on all image data between the forward projection of the three-dimensional image data set and the first and/or second X-ray image. In the determination of the third part of the target function, all image data of the first and/or second X-ray image are used. For example, tissue-to-air transitions, which can represent distinctive structural features, can be used for the method step. The order of method steps V6-1, V6-2 and V6-3 can be varied without impairing the process.

The optimization of the target function can be carried out by applying an iterative method. During each iteration step, the same projective geometry can be assumed for method steps V6-1-V6-3 (all parts of the target function). Subsequently, on the basis of this assumption, all values of the parts of the target function are summed up, taking into account the weighting of the parts of the target function, so as to obtain the value of the target function for a projective geometry. In the further iterations, further projective geometries are then evaluated by the optimization method used and, after reaching a termination criterion, for example reaching the maximum iteration steps, the projective geometry with the optimum value of the target function is presented as the optimum similarity.

In method step V7, if the projective geometry has been successfully determined, provision is made for the two-dimensional live X-ray image to be superimposed in the plane of the X-ray image with the forward-projected vessel structures under the optimum projective geometry. For example, vessel structures with or without a contour or only the contour can be displayed superimposed with the live X-ray image on a display device using the forward projection of the vessel structure model for the optimum projective geometry.

It is possible that the position of the examination zone may also change during the operation, for example due to a change of the imaging geometry of the X-ray machine or due to a shift of the position of the table. These changes can, without readministration of the contrast agent, allow further use of the method, wherein there is the possibility of continuing to use the method according to the present technology, without redetermining the optimum projective geometry, merely by a transformation of the projective geometry that was determined before the imaging geometry. In the event that the imaging geometry changes, encoders, which are position and angle transmitters of the X-ray machine or of the table, can be evaluated and this can be recalculated with the previously determined optimum projective geometry.

In the case in which the new value exceeds the stored threshold value (in the case of a minimization problem) or falls below it (in the case of a maximization problem), for example by a factor to be determined, which can be defined in a program, for example the organ program, the vessel structure or the vessel contour can no longer be displayed on the live X-ray image. If the recalculated values fall below the threshold value again, the vessel structure can be superimposed again. The latter can also be the case when the threshold value is briefly exceeded, for example due to a movement of the operating table, due to a movement of the X-ray machine, or due to contrast agent administration not signaled to the X-ray machine. If the values are no longer under- or overshot within a predefined time interval, which can be set in a program, for example in the organ program, the X-ray machine can provide notification of this and offer the user a new determination of the projective geometry with renewed contrast agent administration or alternatively the changeover to an alternative two-dimensional procedure.

A switch to an alternative two-dimensional representation is illustrated in FIG. 1 as method step V8. In the event that the compared values do not satisfy the corresponding thresholds, the X-ray machine can provide notification of this, for example by displaying a message on the display apparatus. The user can now select the switchover to the 2D process, which also corresponds to method step V8.

The determination of the target function and the optimum projective geometry will be described in more detail with reference to FIG. 2.

Figure 2:
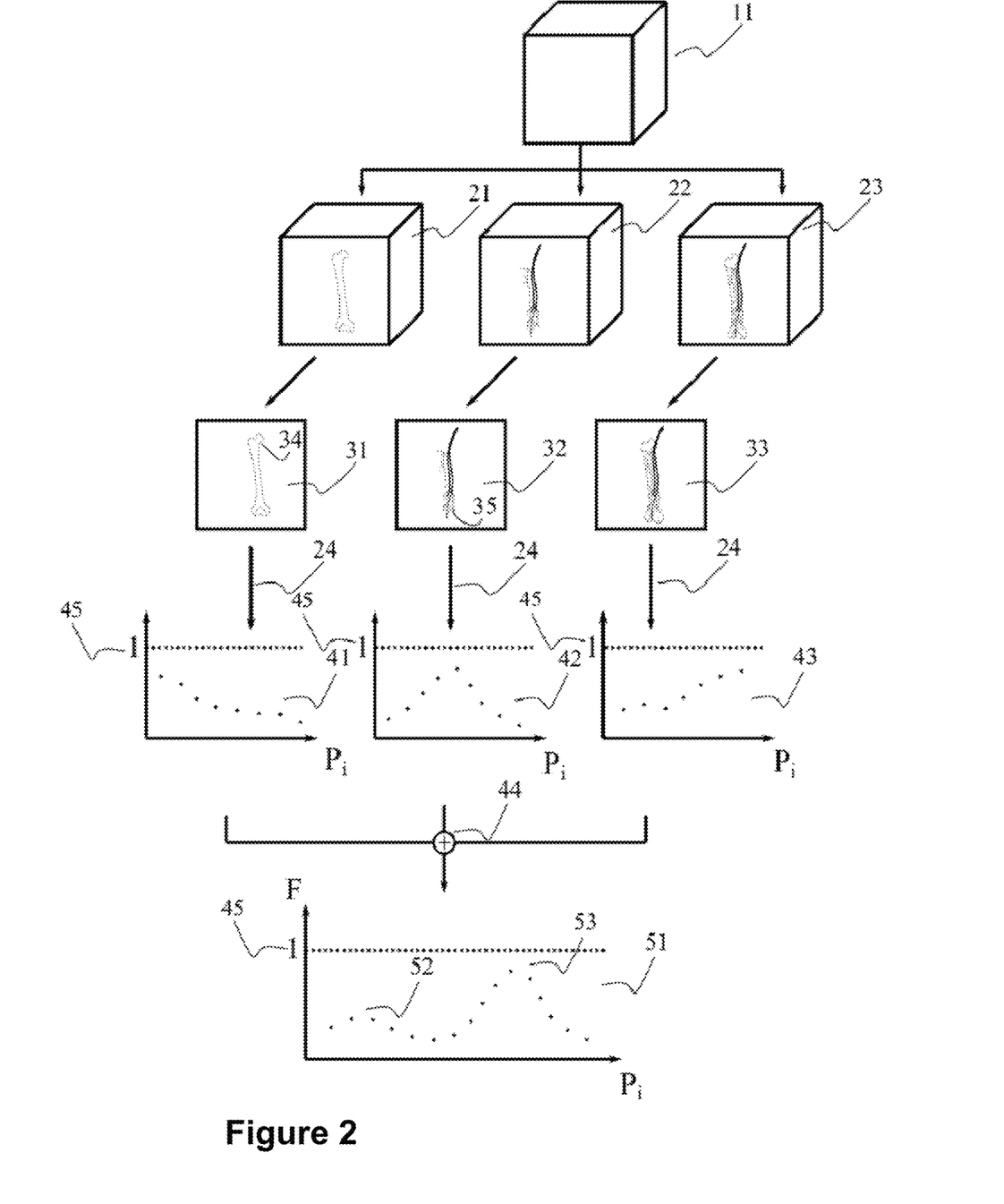
FIG. 2 shows, in an exemplary graphic representation, a determination of the optimum projective geometry between a recorded three-dimensional image data set and the first and/or second X-ray image and the subtraction image.

As shown in FIG. 2, a three-dimensional image data set 11 can first be segmented into a bone structure model 21, a vascular structure model 22, and a third part 23, which contains all image data of the three-dimensional image data set 11. Two-dimensional synthetic forward projections 31, 32, 33 can then be determined from the segmented components and may be compared with the first and/or second X-ray image and the subtraction image by means of a projective geometry 24 ($P_i$) and a similarity can be determined form the comparison for each segmented component 21, 22, 23. The maximum value for determining the similarity 45 can be 1, which corresponds to a complete coincidence of the synthetic forward projection with the first and/or second X-ray image and the subtraction image. The program preferably uses distinctive structural features (e.g., features 34, 35), for example special bone shapes 34 or distinctive vascular branches 35, to determine the similarities.

A subsequent summation 44 of the similarities of the individual segmented portions 21, 22, 23, wherein the similarities of the individual segmented portions 21, 22, 23 can each be weighted by means of a coefficient, yields a value of the target function 51. By means of further iteration steps, some or all three parts of the target function can determine different similarities 41, 42, 43 of the individual segmented parts 21, 22, 23, while varying the projective geometry 24 for each additional projective geometry that is used.

In the further iterations, additional projective geometries are then evaluated by the optimization method used and, after reaching a termination criterion, for example a predetermined threshold value of the target function, the projective geometry with the optimum value of the target function is presented as the optimum similarity. The optimum similarity can be the global maximum 53 of the determined target function 51, it also being possible to determine local extrema 52 in the target function in addition to the global optimum 53.

Other, particularly advantageous embodiments and further developments of the present technology shall become apparent from the dependent claims and the description, where in this case the independent claims of one category of claims can also be further developed analogously to the dependent claims of another category of claims; and, in particular, individual features of different exemplary embodiments or variants can be combined to form new exemplary embodiments or variants.

What is claimed is:

1. A method for processing a three-dimensional image data set with two-dimensional X-ray images captured by an X-ray machine, the method comprising:
    providing a three-dimensional image data set of at least one examination zone in which anatomical structures are present;
    segmenting the three-dimensional image data set to provide a three-dimensional vascular structure model describing a vascular structure and a three-dimensional bone structure model describing a bone structure;
    recording a first two-dimensional X-ray image containing at least a portion of the bone structure and at least a portion of the vascular structure using a recording geometry and in the presence of a first contrast agent concentration;
    recording a second two-dimensional X-ray image of the examination zone, the second two-dimensional X-ray image containing a second contrast agent concentration that is different from the first contrast agent concentration, wherein the recording of the second two-dimensional X-ray image takes place using the same recording geometry as the first two-dimensional X-ray image;
    subtracting the first and second X-ray images to generate a subtraction image, wherein the subtraction image includes the vascular structure;
    determining an optimum projective geometry using a three-part target function, wherein at least a portion of the three-part target function is compared with a pre-settable threshold value criterion; and
    aborting the method and providing an option to a user to switch to an alternative two-dimensional method if the threshold value criterion of the target function is missed,
    wherein a first part of the three-part target function represents a similarity between a forward projection of the bone structure model of the three-dimensional image data set and the bone structure in at least one of the first and second X-ray images, while varying an assumed projective geometry,
    wherein a second part of the three-part target function represents a similarity between a forward projection of the vascular structure model of the three-dimensional image data set and the vascular structure of the subtraction image, while varying the assumed projective geometry, and
    wherein a third part of the three-part target function represents a similarity between all image data of the forward projection of the three-dimensional image data set and all image data of at least one of the first and second X-ray images, while varying the assumed projective geometry.

2. The method of claim 1, wherein the first, second, and third parts of the three-part target function are differently weighted in order to determine the optimum projective geometry.

3. The method of claim 1, wherein determining the optimum projective geometry comprises performing a minimization or a maximization of the three-part target function.

4. The method of claim 1, wherein a digital subtraction angiography is performed and used as the second two-dimensional X-ray image of the examination zone.

5. The method of claim 4, wherein the digital subtraction angiography is combined by a minimum or maximum method.

6. The method of claim 1, wherein the X-ray machine is a C-arm X-ray machine.

7. The method of claim 1, wherein the three-dimensional image data set is recorded by means of computed tomography, magnetic resonance tomography, or a C-arm X-ray machine.

8. The method of claim 1, wherein the three-dimensional image data set is pre-segmented in order to make available a three-dimensional vessel structure and a three-dimensional bone structure.

9. The method of claim 1, further comprising displaying, on a display, a superimposition of a forward projection under the optimum projective geometry with a live X-ray image, wherein the superimposition of the forward projection under the optimum projective geometry with the live X-ray image is no longer shown on the display if one or more of a movement of the X-ray device, a change in the recording geometry of the live X-ray image, or a shift of position of a corresponding patient on a patient bed is detected.

10. The method of claim 9, wherein at least one measurement field is defined in each live X-ray image, the measurement field narrowly delimits a structure which may change over time, and an evaluation is performed for each live X-ray image in such a way that a sum value obtained by addition of all pixel values in the measurement field is monitored and, for a predetermined percentage change in the sum value compared with the sum value of the previous live X-ray image, the superimposition of the forward projection under the optimum projective geometry with the live X-ray image is no longer shown on the display.

11. The method of claim 1, wherein vessel structures with or without a contour or only the contour are displayed superimposed with a live X-ray image on a display device using the forward projection of the vessel structure model in the optimum projection geometry.

12. A method for processing a three-dimensional image data set with two-dimensional X-ray images captured by an X-ray machine, the method comprising:

providing a three-dimensional image data set of at least one examination zone in which anatomical structures are present;

segmenting the three-dimensional image data set to provide a three-dimensional vascular structure model describing a vascular structure and a three-dimensional bone structure model describing a bone structure;

recording a first two-dimensional X-ray image containing at least a portion of the bone structure and at least a portion of the vascular structure using a recording geometry and in the presence of a first contrast agent concentration;

recording a second two-dimensional X-ray image of the examination zone, the second two-dimensional X-ray image containing a second contrast agent concentration that is different from the first contrast agent concentration, wherein the recording of the second two-dimensional X-ray image takes place using the same recording geometry as the first two-dimensional X-ray image;

subtracting the first and second X-ray images to generate a subtraction image, wherein the subtraction image includes the vascular structure;

determining an optimum projective geometry using a three-part target function; and displaying, on a display, a superimposition of a forward projection under the optimum projective geometry with a live X-ray image, wherein the superimposition of the forward projection under the optimum projective geometry with the live X-ray image is no longer shown on the display if one or more of a movement of the X-ray device, a change in the recording geometry of the live X-ray image, or a shift of position of a corresponding patient on a patient bed is detected, wherein at least one measurement field is defined in each live X-ray image, the measurement field narrowly delimits a structure which may change over time, and an evaluation is performed for each live X-ray image in such a way that a sum value obtained by addition of all pixel values in the measurement field is monitored and, for a predetermined percentage change in the sum value compared with the sum value of the previous live X-ray image, the superimposition of the forward projection under the optimum projective geometry with the live X-ray image is no longer shown on the display, wherein a first part of the three-part target function represents a similarity between a forward projection of the bone structure model of the three-dimensional image data set and the bone structure in at least one of the first and second X-ray images, while varying an assumed projective geometry, wherein a second part of the three-part target function represents a similarity between a forward projection of the vascular structure model of the three-dimensional image data set and the vascular structure of the subtraction image, while varying the assumed projective geometry, and wherein a third part of the three-part target function represents a similarity between all image data of the forward projection of the three-dimensional image data set and all image data of at least one of the first and second X-ray images, while varying the assumed projective geometry.

* * * * *